(12) United States Patent
Kobayashi

(10) Patent No.: US 8,858,483 B2
(45) Date of Patent: Oct. 14, 2014

(54) SUPPORTER FOR ACHILLES TENDON

(75) Inventor: Aya Kobayashi, Tokyo (JP)

(73) Assignee: Nippon Sigmax Co., Ltd., Tokyo (JP)

( * ) Notice: Subject to any disclaimer, the term of this patent is extended or adjusted under 35 U.S.C. 154(b) by 0 days.

(21) Appl. No.: 13/641,572

(22) PCT Filed: Mar. 29, 2011

(86) PCT No.: PCT/JP2011/057887
§ 371 (c)(1),
(2), (4) Date: Oct. 25, 2012

(87) PCT Pub. No.: WO2011/129195
PCT Pub. Date: Oct. 20, 2011

(65) Prior Publication Data
US 2013/0035625 A1    Feb. 7, 2013

(30) Foreign Application Priority Data
Apr. 16, 2010 (JP) ................. 2010-095071

(51) Int. Cl.
| | | |
|---|---|---|
| A61F 5/00 | (2006.01) | |
| A61F 13/00 | (2006.01) | |
| A61F 5/01 | (2006.01) | |
| A61F 13/06 | (2006.01) | |
| A41D 13/06 | (2006.01) | |

(52) U.S. Cl.
CPC .............. *A61F 13/06* (2013.01); *A61F 5/0111* (2013.01); *A41D 13/06* (2013.01)
USPC .................... 602/27; 602/23; 602/60; 602/65

(58) Field of Classification Search
CPC ... A61F 5/0585; A61F 5/0111; A61F 5/0193; A61F 13/00; A61F 13/14; A61F 13/061; A61F 13/08; A61F 13/0118; A61F 5/0113; A41D 13/08; A41D 13/082
USPC .......... 602/5, 27–29, 60–65, 54, 23; D24/190–192; D29/100, 101.1, 101.2; 2/16, 20

See application file for complete search history.

(56) References Cited

U.S. PATENT DOCUMENTS 332,727 A * 12/1885 McEwen .................... 602/65
363,516 A *  5/1887 Hackey .................... 602/65
(Continued)

FOREIGN PATENT DOCUMENTS

EP       1 179 325 A1    2/2002
JP       3 101931        10/1991
(Continued)

OTHER PUBLICATIONS

International Search Report Issued Apr. 26, 2011 in PCT/JP11/057887 Filed Mar. 29, 2011.

(Continued)

*Primary Examiner* — Kim M Lewis
(74) *Attorney, Agent, or Firm* — Oblon, Spivak, McClelland, Maier & Neustadt, L.L.P.

(57) ABSTRACT

Provided is an Achilles tendon support capable of suppressing a dorsiflexion of an ankle joint as well as suppressing a twist of the ankle joint. The Achilles tendon support includes: an inner support section for covering an Achilles tendon and both side edge portions thereof, upper portions of the inner support section being fastenable to each other on a front side of an upper ankle portion with a hook and loop fastener; and an outer support section for covering the Achilles tendon and both the side edge portions thereof in a range from a sole through a back heel portion, upper portions of the outer support section being fastenable to an outer surface of the inner support section with a hook and loop fastener.

5 Claims, 4 Drawing Sheets

(56) References Cited

U.S. PATENT DOCUMENTS

| | | | | |
|---|---|---|---|---|
| 540,931 | A * | 6/1895 | Walkey | 602/65 |
| 672,146 | A * | 4/1901 | Collis | 602/65 |
| 913,263 | A * | 2/1909 | Collis | 602/65 |
| 938,440 | A * | 10/1909 | Sescila | 602/65 |
| 3,515,136 | A * | 6/1970 | Baker | 602/65 |
| 4,841,957 | A | 6/1989 | Wooten et al. | |
| 4,844,058 | A * | 7/1989 | Vogelbach | 602/27 |
| 5,135,473 | A * | 8/1992 | Epler et al. | 602/62 |
| 5,795,316 | A * | 8/1998 | Gaylord | 602/27 |
| 6,022,332 | A * | 2/2000 | Nelson | 602/27 |
| 6,032,286 | A * | 3/2000 | Thomas et al. | 2/22 |
| 7,681,254 | B2 * | 3/2010 | Lambertz | 2/239 |
| 7,993,295 | B2 * | 8/2011 | Nelson | 602/27 |
| 8,230,525 | B2 * | 7/2012 | Lambertz | 2/239 |
| 2003/0204157 | A1 | 10/2003 | Cropper | |
| 2007/0033710 | A1 | 2/2007 | Lambertz | |

FOREIGN PATENT DOCUMENTS

| | | |
|---|---|---|
| JP | 2002 339123 | 11/2002 |
| JP | 2006 505704 | 2/2006 |
| JP | 2008 173179 | 7/2008 |
| JP | 2009 114577 | 5/2009 |
| WO | WO 8702885 A1 * | 5/1987 |

OTHER PUBLICATIONS

Extended European Search Report issued on Mar. 28, 2014 in the corresponding European Application No. 11768716.0.

* cited by examiner

SUPPORTER FOR ACHILLES TENDON

FIELD OF THE INVENTION

The present invention relates to an Achilles tendon support.

BACKGROUND OF THE INVENTION

Conventionally, people who suffer from Achilles tendon disorder such as Achilles tendon rupture or Achilles tendonitis, have generally worn, for example, a support for compressing the entire ankle joint region or a support for preventing ankle joint sprain, when they have a daily life or play sports. However, the conventional supports merely employ a stretchable fabric to compress and secure the ankle joint region, and hence there is a problem in that a dorsiflexion of the ankle joint (movement of raising a toe, that is, movement of stretching the Achilles tendon under stress) cannot be suppressed.

Further, there has been known a sock having spacer cushions arranged in the Achilles tendon region (see, for example, Patent Document 1). However, the sock is merely configured to form a predetermined space between the Achilles tendon and a shoe, and hence the sock can never actually suppress the dorsiflexion of the ankle joint.

PRIOR ART DOCUMENT

Patent Document

[Patent Document 1] JP-A 2006-505704

SUMMARY OF THE INVENTION

Problems to Be Solved

The present invention has been made in view of the above-mentioned conventional problems and circumstances, and it is therefore an object thereof to provide an Achilles tendon support capable of suppressing a dorsiflexion of an ankle joint as well as preventing a twist of the ankle joint.

Means for Solving Problems

The inventor of the present invention has pursued various studies to achieve the above-mentioned object, and eventually found that significantly great effect are obtained with a dual structure including an inner support section for covering and securing an Achilles tendon region, and an outer support section for covering the Achilles tendon region in a range from a sole through a back heel portion, the outer support section being fastenable while being pulled upward. Thus, the present invention has been attained.

That is, according to the present invention, there is provided an Achilles tendon support, including: an inner support section for covering an Achilles tendon and both side edge portions thereof, upper portions of the inner support section being fastenable to each other on a front side of an upper ankle portion with a hook and loop fastener; and an outer support section for covering the Achilles tendon and both the side edge portions thereof in a range from a sole through a back heel portion, upper portions of the outer support section being fastenable to an outer surface of the inner support section with a hook and loop fastener. Thus, the above-mentioned object is achieved.

Effects of the Invention

With the Achilles tendon support of the present invention, the Achilles tendon region is covered with the inner support section and the outer support section in the dual structure. Accordingly, the twist of the ankle joint can be prevented due to a synergistic effect obtained by the inner support section and the outer support section. Further, the upper portions of the outer support section are fastenable to the outer surface of the inner support section while being pulled upward, and accordingly the dorsiflexion of the ankle joint can be suppressed.

Therefore, people who suffer from Achilles tendon disorder can have their daily life and enjoy sports without anxiety, by attaching the Achilles tendon support according to the present invention.

EMBODIMENT FOR CARRYING OUT THE INVENTION

Hereinafter, an embodiment of the present invention is described with reference to the drawings.

Figure 1:
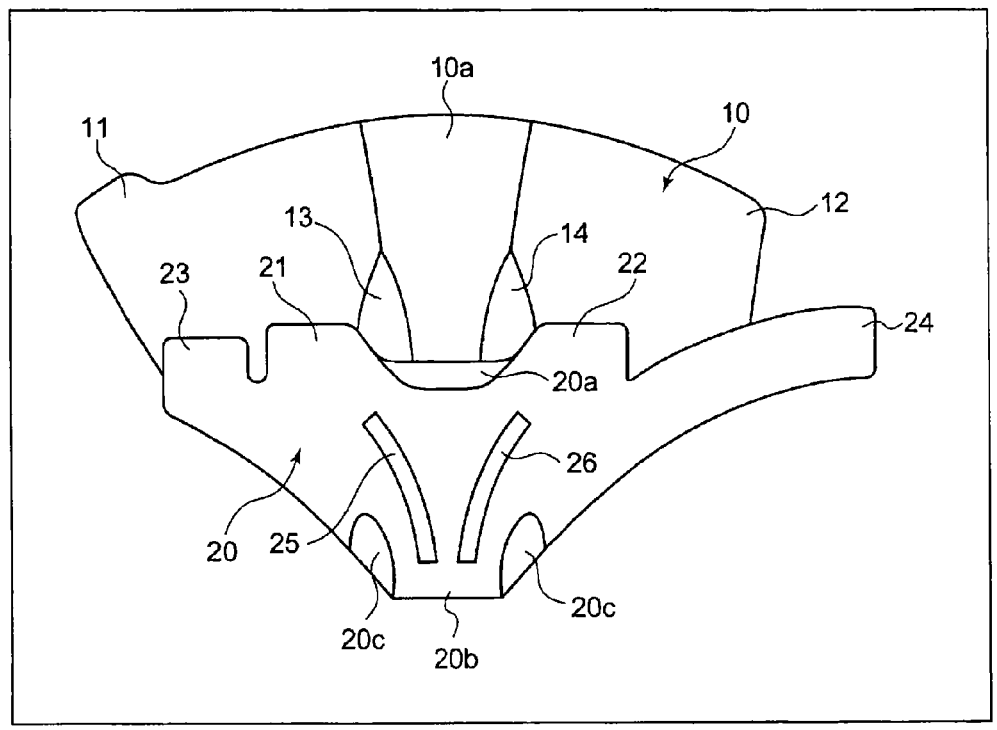
FIG. 1 An explanatory view illustrating an outer-side structure of an Achilles tendon support in a development state according to the present invention.
Figure 2:
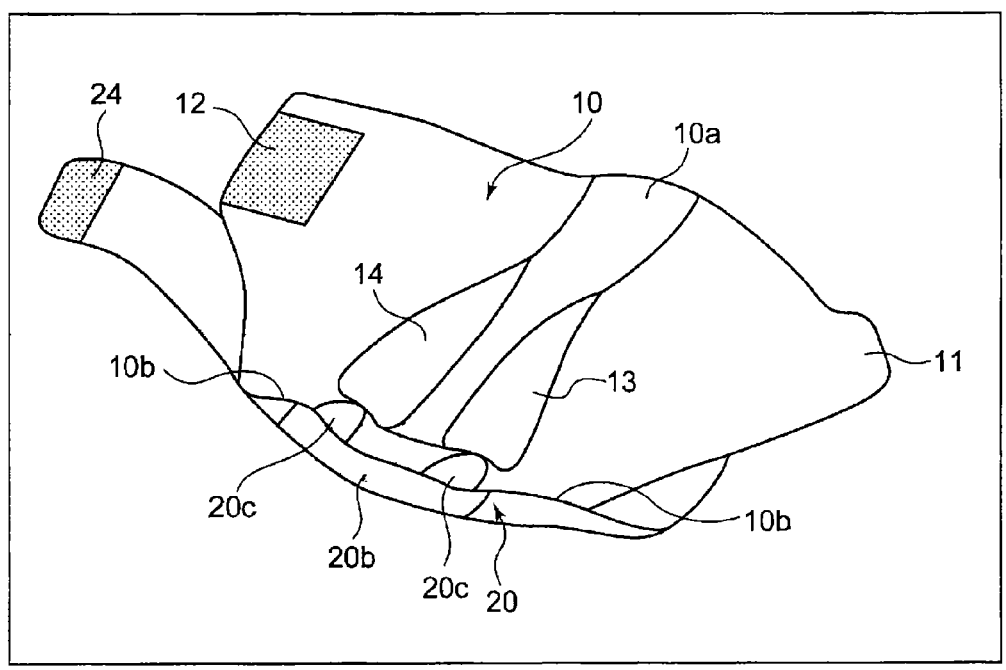
FIG. 2 An explanatory view illustrating an inner-side structure of the Achilles tendon support in the development state according to the present invention.
Figure 4:
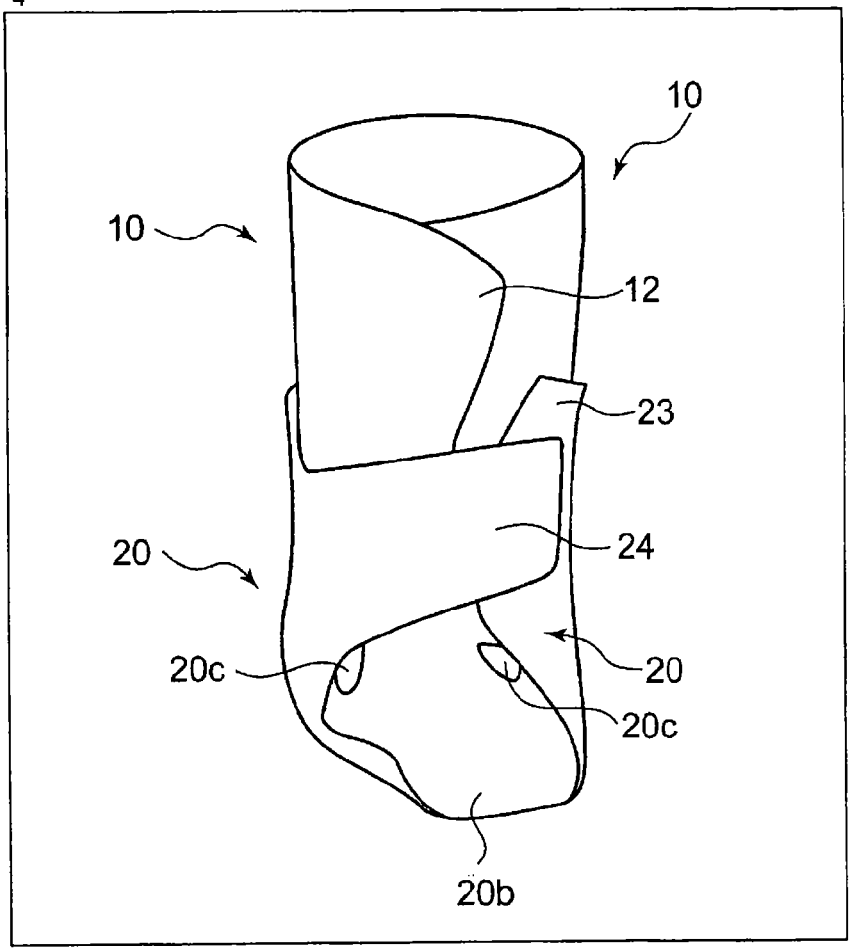
FIG. 4 An explanatory perspective view illustrating the Achilles tendon support in a shaped state according to the present invention.
Figure 5:
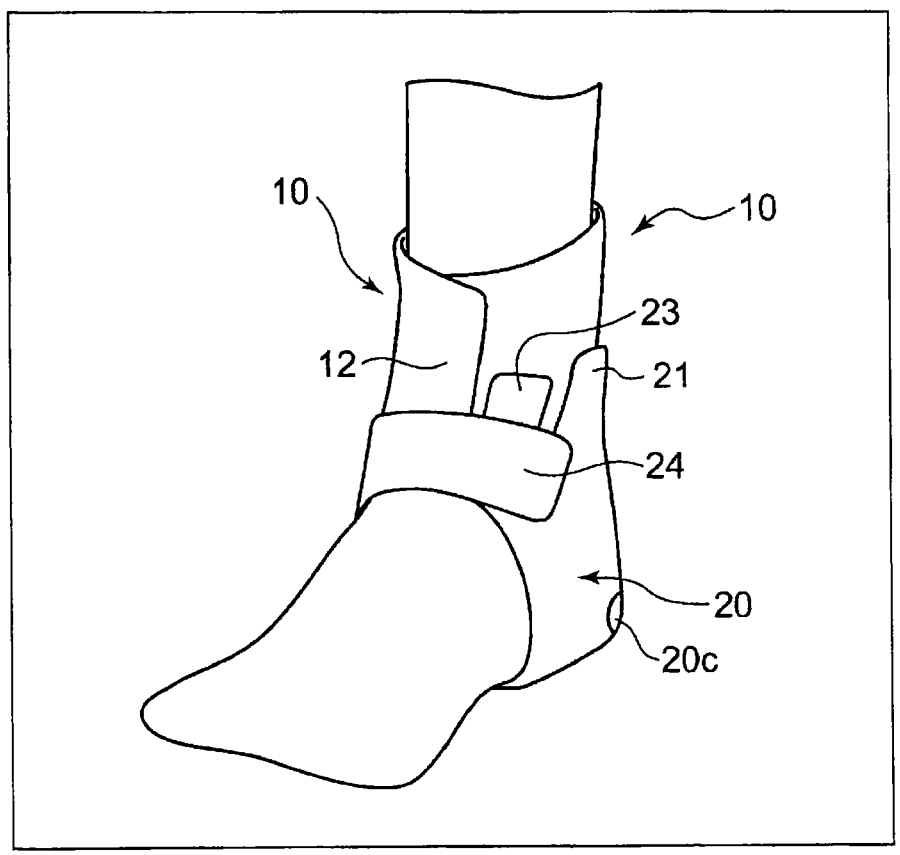
FIG. 5 An explanatory front perspective view illustrating the Achilles tendon support in a use state according to the present invention.

In the figures, 10 denotes an inner support section, which is entirely made of a fabric stretchable by a smaller force than an outer support section 20 described later, and is made of a fabric stretchable by an even smaller force in an Achilles tendon abutment region 10a situated at a center portion thereof. Accordingly, the inner support section 10 covers an Achilles tendon and both side edge portions thereof without applying a large compressing force to the Achilles tendon. As illustrated in FIGS. 1 and 2, fastening pieces 11 and 12 are formed at both upper ends of the inner support section 10, and as illustrated in FIGS. 4 and 5, the fastening pieces 11 and 12 are fastenable to each other on a front side of an upper ankle portion with a hook and loop fastener.

Further, as illustrated in FIGS. 1 and 2, pads 13 and 14, which are each made of a cushion member, are arranged and formed at portions of the inner support section 10 along both sides of the Achilles tendon. With the pads 13 and 14, both sides of the Achilles tendon are supported, and hence an orthostatic state (stability) of the Achilles tendon is improved.

20 denotes the outer support section, which is made of a fabric stretchable by a larger force than the above-mentioned inner support section 10, and covers the Achilles tendon and both the side edge portions thereof in a range from a sole through a back heel portion. At an upper edge portion of the outer support section 20, as illustrated in FIG. 1, projecting hook and loop fastener pieces 21 and 22 are formed so as to avoid an abutting against the Achilles tendon, that is, so as to project slightly outward at both side portions of the Achilles tendon. With the hook and loop fastener, the projecting hook and loop fastener pieces 21 and 22 are detachably fastenable to an outer surface of the inner support section 10. Further, a part 20*a* of the upper edge portion of the outer support section 20, which is situated between the projecting hook and loop fastener pieces 21 and 22 and crosses the Achilles tendon, is made of a fabric stretchable by an even smaller force similarly to the Achilles tendon abutment region 10*a*. Accordingly, a large compressing force is not applied to an upper portion of the Achilles tendon.

When the projecting hook and loop fastener pieces 21 and 22 are grasped and fastened respectively to the outer surface of the inner support section 10 while being pulled obliquely upward, the outer support section 20 is entirely pulled upward to be secured under a state in which the outer support section 20 wraps the range from the sole to the heel. Thus, a more significant effect of suppressing a dorsiflexion of an ankle joint can be obtained. Further, the projecting hook and loop fastener pieces 21 and 22 do not abut against the Achilles tendon so that direct application of pressure to the Achilles tendon can be avoided, and the projecting hook and loop fastener pieces 21 and 22 project slightly outward so that a downward positional movement of the inner support section 10 can be suppressed when being attached.

Further, as illustrated in FIGS. 1 and 4, a projecting hook and loop fastener piece 23 is formed at one end of the upper edge portion of the outer support section 20, and a belt piece 24 is formed at the other end thereof so as to be detachably fastened to an outer surface of the projecting hook and loop fastener piece 23 with a hook and loop fastener while being passed around an ankle. With the projecting hook and loop fastener piece 23 and the belt piece 24, the outer support section 20 can be pulled up toward a top of the foot to be secured under a state in which the heel is wrapped. Thus, varus and valgus of a heel bone (deflection under twisting stress applied to the Achilles tendon) can be suppressed more effectively.

Figure 6:
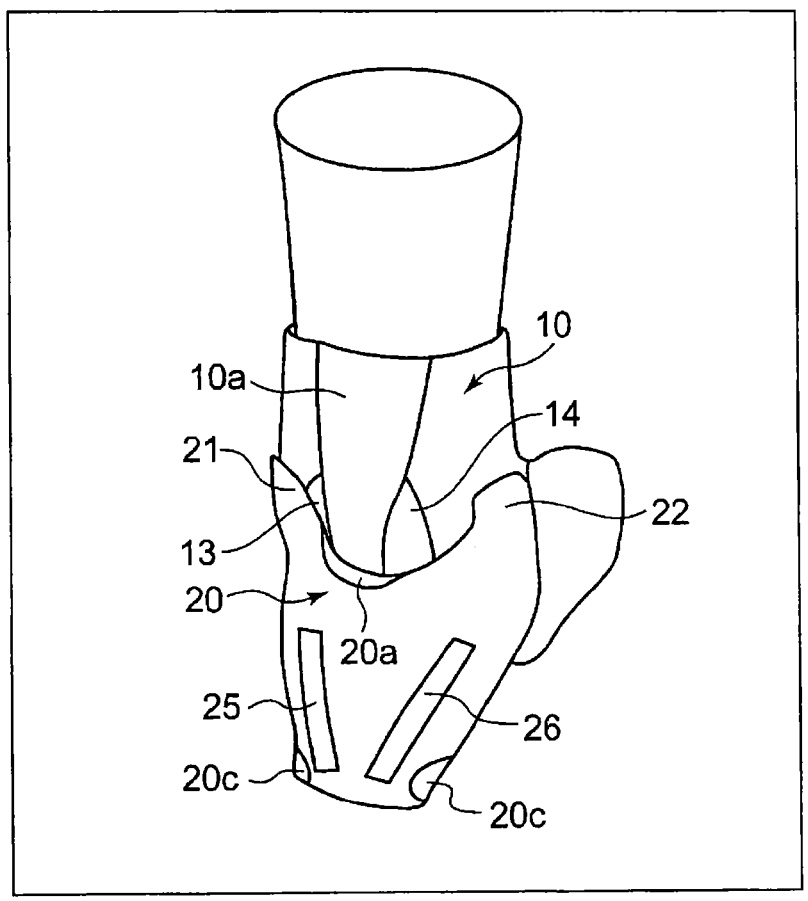
FIG. 6 An explanatory rear perspective view illustrating the Achilles tendon support in the use state according to the present invention.

Further, as illustrated in FIGS. 1 and 6, non-stretchable portions 25 and 26 are arranged and formed into a substantially V-shape at portions of the outer support section 20 along both sides of the Achilles tendon. There is no particular limitation to a specific method of forming the non-stretchable portion 25. For example, a simple method therefor is sewing of a non-stretchable fabric. With the non-stretchable portions 25 and 26, a force for suppressing the dorsiflexion of the ankle joint can further be increased.

Further, at both side portions of the outer support section 20 which abut against the heel, holes 20*c* are formed as illustrated in FIGS. 1 and 6. With the holes 20*c*, a warpage of the heel portion can be prevented when being attached, with the result that the outer support section 20 can be pulled upward to be secured more effectively.

Figure 3:
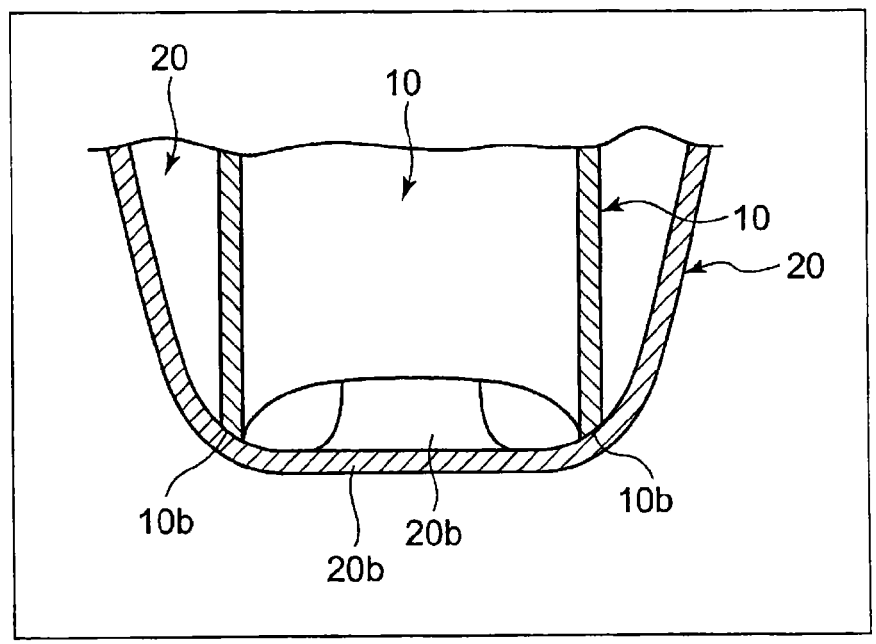
FIG. 3 An explanatory enlarged sectional view illustrating a main part of a coupling portion for an inner support section and an outer support section.

As illustrated in FIG. 3, the above-mentioned inner support section 10 and outer support section 20 are coupled to each other by means of, for example, sewing a part of a lower portion 10*b* of the inner support section 10 to both side parts of a sole covering piece portion 20*b* of the outer support section 20.

Next, description is given of a method of using the Achilles tendon support according to the above-mentioned embodiment of the present invention.

First, a foot is inserted from a heel into the support in a development state (see FIG. 2), and a sole is placed on the sole covering piece portion 20*b* of the outer support section 20. Subsequently, an Achilles tendon and both side edge portions thereof are covered with the inner support section 10, and in this state, the fastening pieces 11 and 12 are fastened to each other on a front side of an upper ankle portion. Subsequently, the projecting hook and loop fastener pieces 21 and 22 of the outer support section 20 are grasped and fastened respectively to the outer surface of the inner support section 10 while being pulled obliquely upward. Then, the projecting hook and loop fastener piece 23 of the outer support section 20 is grasped and fastened to the outer surface of the inner support section 10 while being pulled up toward a top of the foot. After that, the belt piece 24 of the outer support section 20 is grasped and fastened to the outer surface of the projecting hook and loop fastener piece 23 (including the inner support section on the periphery thereof) while being pulled toward the other side so as to be looped around an ankle. Consequently, an attached use state as illustrated in FIGS. 4 and 5 is attained.

LIST OF REFERENCE NUMBERS

10: inner support section
10*a*: Achilles tendon abutment region
10*b*: lower portion
11: fastening piece
12: fastening piece
13: pad
14: pad
20: outer support section
20*a*: part crossing Achilles tendon
20*b*: sole covering piece portion
20*c*: hole
21: fastener piece
22: fastener piece
23: fastener piece
24: belt piece
25: non-stretchable portion
26: non-stretchable portion

The invention claimed is:

1. An Achilles tendon support, comprising:
an inner support section for covering an Achilles tendon and both side edge portions thereof, upper portions of the inner support section being fastenable to each other on a front side of an upper ankle portion with a hook and loop fastener;
an outer support section for further covering the Achilles tendon and both the side edge portions thereof in a range from a sole through a back heel portion, upper portions of the outer support section being fastenable to an outer surface of the inner support section with a hook and loop fastener; and
non-stretchable portions arranged and formed into a substantially V-shape at portions of the outer support section for covering both sides of the Achilles tendon.

2. The Achilles tendon support according to claim 1, wherein the inner support section is made of a fabric stretchable by a smaller force than the outer support section.

3. The Achilles tendon support according to one of claims 1 or 2, further comprising pads arranged and formed at portions of the inner support section along both sides of the Achilles tendon.

4. The Achilles tendon support according to one of claims 1 or 2, further comprising projecting hook and loop fastener pieces formed at an upper edge portion of the outer support section so as to avoid abutting against the Achilles tendon.

5. The Achilles tendon support according to one of claims 1 or 2, further comprising:
a projecting hook and loop fastener piece formed at one end of the upper edge portion of the outer support section; and a belt piece formed at the other end of the upper edge portion of the outer support section so as to be fastened to an outer surface of the projecting hook and loop fastener piece with a hook and loop fastener while being passed around an ankle.

\* \* \* \* \*